United States Patent [19]

Stumpp et al.

[11] Patent Number: 5,059,715
[45] Date of Patent: Oct. 22, 1991

[54] PREPARATION OF BIS(4-HYDROXYPHENYL)SULFONE

[75] Inventors: Michael Stumpp, Deidesheim; Peter Neumann, Mannheim; Wolfgang Ruehenback, Birkenau; Michael Bergner, Frankenthal, all of Fed. Rep. of Germany

[73] Assignee: BASF Aktiengesellschaft, Ludwigshafen, Fed. Rep. of Germany

[21] Appl. No.: 668,328

[22] Filed: Mar. 14, 1991

Related U.S. Application Data

[63] Continuation of Ser. No. 413,585, Sep. 28, 1989, abandoned.

[30] Foreign Application Priority Data

Oct. 19, 1988 [DE] Fed. Rep. of Germany ....... 3835527

[51] Int. Cl.⁵ .............................................. C07C 315/04
[52] U.S. Cl. .................................................... 568/33
[58] Field of Search ......................................... 568/33

[56] References Cited

U.S. PATENT DOCUMENTS

| | | | |
|---|---|---|---|
| 3,065,274 | 11/1962 | Vegter et al. | 568/33 |
| 3,297,766 | 1/1967 | Bradley et al. | 568/33 |
| 4,162,270 | 7/1979 | Ogata et al. | 568/33 |

FOREIGN PATENT DOCUMENTS

| | | | |
|---|---|---|---|
| 220004 | 4/1987 | European Pat. Off. | |
| 293037 | 11/1988 | European Pat. Off. | |
| 1618023 | 8/1971 | Fed. Rep. of Germany | |
| 2708388 | 8/1978 | Fed. Rep. of Germany | |
| 1276779 | 10/1961 | France | |
| 2030566 | 4/1980 | United Kingdom | |
| 2088858 | 6/1982 | United Kingdom | 568/33 |

OTHER PUBLICATIONS

Houben–Weyl, Methoden der Organischen Chemie, vol. 9, p. 494 to 497, 1955.
Derwent Abstract of Japanese Patent 50-106,938 Published Aug. 1975.

*Primary Examiner*—Mary E. Ceperley
*Attorney, Agent, or Firm*—Oblon, Spivak, McClelland, Maier & Neustadt

[57] ABSTRACT

A process for the preparation of bis(4-hydroxyphenyl)-sulfone by reacting phenol with sulfuric acid in the presence of a solvent at from 130° to 220° C. and in the presence or absence of a sulfonating assistant, wherein the bis(4-hydroxyphenyl)sulfone formed is selectively deposited on a nucleating surface during or after the reaction, and thus removed from the reaction medium.

8 Claims, No Drawings

PREPARATION OF BIS(4-HYDROXYPHENYL)SULFONE

This application is a continuation of application Ser. No. 413,585, filed on Sept. 28, 1989, now abandoned.

The present invention relates to a novel process for the preparation of bis(4-hydroxyphenyl)sulfone of high purity, by reacting phenol with sulfuric acid in the presence of a solvent and in the presence or absence of a sulfonating assistant, in which process bis(4-hydroxyphenyl)sulfone is deposited on a surface, during or after the reaction, and thus removed from the reaction medium.

Bis(4-hydroxyphenyl)sulfone is of great commercial interest for the preparation of fibers, resins and highly heat-resistant plastics (for example polyethersulfones). Since the properties of the polymers prepared from bis(4-hydroxyphenyl)sulfone are highly dependent on the purity of the monomers, selective synthesis processes for bis(4-hydroxyphenyl)sulfone are in demand.

Bis(4-hydroxyphenyl)sulfone can be prepared by reacting phenol with sulfuric acid, without using a solvent. These processes give a crude product which alongside 60–70% of bis(4-hydroxyphenyl)sulfone contains 20–30% of the isomer 2,4,-dihydroxydiphenylsulfone and about 10% of the "trimer" 6-hydroxy[1,3-bis(4-hydroxyphenylsulfonyl]benzene. All these processes require major effort if bis(4-hydroxyphenyl)sulfone is to be isolated in high purity from the mixture.

Both the yield and the selectivity of the reaction can be improved by using a solvent, as is demonstrated by the Examples in JP-A-106,938/1975 or in U.S. Pat. No. 4,162,270.

According to DE-A-2,708,388, the reaction of phenol with sulfuric acid in the presence of a solvent, e.g. of an aromatic hydrocarbon, gives bis(4-hydroxyphenyl)sulfone and the isomeric 2,4,-dihydroxydiphenylsulfone in a ratio of about 3:1. In addition, as our own experiments have shown, a small amount of 6-hydroxy[1,3-bis(4-hydroxyphenylsulfonyl)]benzene is formed. The yield and purity of the target product are improved by continuously removing the solvent from the reaction by distillation or by distilling off the product after the reaction has been substantially completed, it being important to carry out the distillation in the temperature range of 160°–200° C., since only under these conditions is isomerization of the 2,4'-isomer to bis(4-hydroxyphenyl)sulfone achieved.

Finally, according to the teaching of EP-A-220,004 phenol and sulfuric acid may be reacted in an inert solvent at from 160° to 200° C., with bis(4-hydroxyphenyl)sulfone being removed from the reaction medium by selective crystallization. For this, however, it is necessary to predetermine precisely the amount of inert solvent in order to ensure that throughout the course of the reaction the medium remains constantly saturated in bis(4-hydroxyphenyl)sulfone and constantly unsaturated in 2,4'-dihydroxydiphenylsulfone.

It is an object of the present invention to provide a selective process for the preparation of bis(4hydroxyphenyl)sulfone of high purity from phenol and sulfuric acid. The process is required to give the product in a purity of better than 99% without demanding expensive separation or purification stages.

We have found that this object is achieved and that the preparation of bis(4-hydroxyphenyl)sulfone by reacting phenol with sulfuric acid in the presence of a solvent at from 130° to 220° C. and in the presence or absence of a sulfonating assistant, may be carried out advantageously if the bis(4-hydroxyphenyl)sulfone formed is selectively deposited on a nucleating surface during or after the reaction, and thus removed from the reaction medium.

In the process according to the invention it is advantageous not to introduce the sulfuric acid initially with the phenol, as is customary in the prior art, and to heat the mixture, but instead to meter the sulfuric acid continuously or in portions into the reaction mixture, consisting of phenol and solvent, with or without sulfonating assistant, over the course of the reaction, especially during or after the heating stage. In this way it is possible so to control the reaction that the undesired formation of 6-hydroxy-[1,3-bis(4-hydroxyphenylsulfonyl)]-benzene is substantially repressed. Furthermore, the selective crystallization of the bis(4-hydroxyphenyl)sulfone can be effectively controlled, since at no time a two-phase liquid-liquid system is formed.

Suitable solvents are either excess phenol or an inert solvent, for example an aliphatic, cycloaliphatic, araliphatic or aromatic hydrocarbon, e.g. benzene, toluene, xylene, ethylbenzene, diethylbenzene, decalin or tetralin, a haloalkane, e.g. tetrachloroethane, a halogenated aromatic hydrocarbon, e.g. chlorobenzene, dichlorobenzene or trichlorobenzene, or a mixture of these. Preferred solvents are those in which the 2,4'-isomer is more highly soluble than the bis(4-hydroxyphenyl)sulfone. Examples of such solvents in which there is a major difference in solubility between the two isomers are chlorobenzene, dichlorobenzene and trichlorobenzene.

If excess phenol is used as the solvent, an 0.1-fold to 5-fold excess of phenol, based on the amount by weight of sulfuric acid, is as a rule introduced initially and the sulfuric acid is then added as described above.

When an inert solvent is used, its amount is in general about 0.1-fold to 5-fold, preferably 0.3-fold to 3-fold, the amount by weight of the phenol employed. Larger amounts of solvent can be used, but are not advantageous.

The amounts of phenol and sulfuric acid to be used are not particularly critical and lie within the range known from the prior art. In general, not less than 2 moles of phenol are used per mole of sulfuric acid.

The sulfonation can be carried out in the presence or absence of sulfonating assistants, such as boron trifluoride or boric acid, which are known from the prior art, e.g. Houben-Weyl, Methoden der Organischen Chemie, Volume IX, pages 494–497 (1955). Catalytic amounts of the assistant suffice as a rule.

According to the invention, the bis(4-hydroxyphenyl)sulfone formed is withdrawn from the reaction mixture by deposition on a nucleating surface, resulting in an increase in the yield of bis(4-hydroxyphenyl)sulfone by shifting the reaction equilibrium, and giving a product which is more than 99% pure. The 2,4'-dihydroxydiphenylsulfone which is far more readily soluble, for example from 50 to 100 times as soluble, in the above solvents remains in the solution and deposits, also as bis(4-hydroxyphenyl)sulfone, after isomerization at a temperature which is advantageously above 160° C.

For the purposes of the invention, a nucleating surface is in particular to be understood as a supercooled surface. A nucleating surface which is at a temperature about 10–50 degrees below the reaction temperature is particularly preferred. Surface materials suitable for the deposition are, for example, metal, glass, ceramic or heat-resistant inert plastic surfaces. Specific examples are surfaces of steel, glass, enamels or Teflon.

It is furthermore possible to roughen the surface to improve nucleation. This may be done, for example, by etching, scoring, scratching or sanding.

The crystallization on the surfaces described can be further assisted by seeding the reaction mixture with foreign crystals or, advantageously, with crystals of the pure product.

The selective crystallization can advantageously be carried out in accordance with two procedures which differ in principle. On the one hand, the crystallization medium described above can be present in situ in the reaction mixture, i.e. the sulfonation is carried out directly in the presence of the roughened and/or supercooled surface. Alternatively, the crystallization medium can be located externally and the reaction mixture is circulated over this medium, for example in the form of a cooling coil or of a scraper cooler.

The target product can, in either method, be removed continuously or batchwise. For example, the solid can be separated off mechanically or be dissolved off by means of a solvent.

The process according to the invention can advantageously be carried out as follows: the phenol, with or without inert solvent and with or without sulfonating assistant is introduced into the reaction vessel and heated to 130°–220° C., preferably 160°–200° C. During heating, or thereafter, concentrated sulfuric acid is added dropwise, with the water formed being removed from the system in a conventional manner and the solvent being recycled continuously to the reaction mixture.

During the reaction, bis(4-hydroxyphenyl)sulfone deposits selectively on the external or internal crystallization medium. After completion of the reaction the mixture can be stirred further, advantageously at above 160° C., in order to effect complete isomerization of the 2,4'-dihydroxybiphenylsulfone present in the solution. The solid is separated out of the reaction mixture in a manner known per se, so that further comments are not required.

For further purification—which is often unnecessary—the product can be taken up in an aqueous alkali solution and can, if appropriate after the solution has been treated with active charcoal and been filtered, be reprecipitated with acids, e.g. mineral acids, especially sulfuric acid, at a pH of about 6–7.

In continuous operation, the procedure can advantageously be as above, except that the phenol and sulfuric acid are added, in a molar ratio of 2:1, to the reaction medium at the rate at which they react to form bis(4-hydroxy-phenyl)sulfone. In this embodiment, the target product is of course also removed continuously.

The bis(4-hydroxyphenyl)sulfone prepared by the process according to the invention is more than 99% pure.

The Examples which follow illustrate the invention.

EXAMPLE 1

385 g (4.1 moles) of phenol, 150 ml of chlorobenzene and 60 ml of o-dichlorobenzene were introduced under nitrogen into a 2 liter ground-flange vessel equipped with a glass cooling coil, and were refluxed. 209 g (2.05 moles) of 96% strength by weight sulfuric acid were added dropwise over 2 hours. Throughout the reaction time, water was removed from the system and the organic phase recycled to the reaction vessel. The temperature of the cooling coil was then dropped to about 135° C. while the temperature of the reaction medium was about 168° C., whereupon bis(4-hydroxyphenyl)sulfone began to deposit on the cooling coil. Stirring was continued for 1.5 hours at 168° C., after which the cooling coil was removed, the precipitate formed was taken up in aqueous alkali solution, the solution was treated with active charcoal and filtered and the product was reprecipitated with sulfuric acid at pH 6.5. After drying, bis(4-hydroxyphenyl)sulfone was obtained in a purity of >99.5% (HPLC) and in a yield of 70% based on sulfuric acid employed.

EXAMPLE 2

385 g (4.1 moles) of phenol, 150 ml of chlorobenzene and 60 ml of o-dichlorobenzene were introduced under nitrogen into a 2 liter ground-flange vessel arranged in a circuit with a scraper cooler, and were refluxed. 209 g (2.05 moles) of 96% strength by weight sulfuric acid were added dropwise over 2 hours. Throughout the reaction time, water was removed from the system and the organic phase was recycled to the reaction vessel. The entire reaction solution (at 168° C.) was then pumped, in a closed heated system, over the scraper cooler (at 100° C.) and back into the reaction vessel. The product which deposited on the supercooled cooler was scraped off continuously and removed After a reaction time of 3 hours, bis(4-hydroxyphenyl)sulfone was obtained in a purity of >99.5% (HPLC) and in 90% yield. To effect further purification, the procedure described in Example 1 may be followed.

EXAMPLE 3

385 g (4.1 moles) of phenol, 150 ml of chlorobenzene and 60 ml of o-dichlorobenzene were introduced under nitrogen into a 2 liter ground-flange vessel arranged in circuit with a scraper cooler, and were refluxed. 209 g (2.05 moles) of 96% strength by weight sulfuric acid were added dropwise over 2 hours. Throughout the reaction time, water was removed from the system and the organic phase was recycled to the reaction vessel. The entire reaction solution (at 168° C.) was then pumped, in a closed heated system, over the scraper cooler (at 100° C.) and pumped back into the reaction medium via a filter unit which could be discharged continuously. The bis(4-hydroxyphenyl)sulfone retained in the filter unit was discharged continuously. To maintain the material flow, phenol and sulfuric acid were added to the reaction medium in amounts corresponding to the amount of bis(4hydroxyphenyl)sulfone removed. After a reaction time of 10 hours, a total of 1650 g of bis(4-hydroxyphenyl)sulfone was obtained (yield 89%).

The table which follows shows the course of the reaction.

| Reaction time | Starting materials | | Target product |
|---|---|---|---|
| | Sulfuric acid | Phenol | |
| 3 h | 209 g (2.05 moles) | 365 g (4.1 moles) | 450 g (1.8 moles) |
| 4 h | 306 g (3.0 moles) | 534 g (6 moles) | 650 g (2.6 moles) |
| 10 h | 754 g (7.4 moles) | 1317 g (14.8 moles) | 1650 g (6.6 moles) |

We claim:

1. In a process for the preparation of bis(4-hydroxyphenyl)sulfone by reacting phenol with sulfuric acid in the presence of a solvent at from 130° to 220° C. and in the presence or absence of a sulfonating assistant, the improvement comprising selectively crystallizing the bis(4-hydroxyphenyl)sulfone formed on a nucleating supercooled surface during or after the reaction, and removing the crystallized bis(4-hydroxyphenyl)sulfone selectively deposited on the nucleating supercooled surface from the reaction medium.

2. The process as claimed in claim 1, wherein the solvent used is an aliphatic, cycloaliphatic, aromatic or araliphatic hydrocarbon or hydrocarbon mixture.

3. The process as claimed in claim 1, wherein the nucleating supercooled surface is a roughened surface.

4. The process as claimed in claim 1, wherein crystallization of the bis(4-hydroxyphenyl)sulfone is further assisted by seeding of the nucleating supercooled surface.

5. The process as claimed in claim 1, wherein the nucleating supercooled surface is present in the reactive mixture.

6. The process as claimed in claim 5, wherein the nucleating supercooled surface is a cooling coil.

7. The process as claimed in claim 1, wherein the nucleating supercooled surface is located externally of the reaction zone and the reaction mixture is circulated over the nucleating supercooled surface.

8. The process as claimed in claim 7, wherein the nucleating supercooled surface is a scraper cooler.

* * * * *

UNITED STATES PATENT AND TRADEMARK OFFICE
CERTIFICATE OF CORRECTION

PATENT NO. : 5,059,715

DATED : October 22, 1991

INVENTOR(S) : Michael Stumpp et al.

It is certified that error appears in the above-identified patent and that said Letters Patent is hereby corrected as shown below:

On title page, item [75], third inventor, should read;

--Wolfgang Ruehenbeck--.

Signed and Sealed this

Ninth Day of March, 1993

*Attest:*

STEPHEN G. KUNIN

*Attesting Officer*     Acting Commissioner of Patents and Trademarks